US008702949B2

(12) United States Patent
Ohura et al.

(10) Patent No.: US 8,702,949 B2
(45) Date of Patent: Apr. 22, 2014

(54) CAPILLARY ELECTROPHORESIS APPARATUS

(75) Inventors: Takeshi Ohura, Hitachinaka (JP); Ryoji Inaba, Hitachinaka (JP); Manabu Akiba, Mito (JP); Takashi Gomi, Hitachinaka (JP); Mari Kotoura, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/263,040

(22) PCT Filed: Apr. 8, 2010

(86) PCT No.: PCT/JP2010/056357
§ 371 (c)(1),
(2), (4) Date: Oct. 5, 2011

(87) PCT Pub. No.: WO2010/117032
PCT Pub. Date: Oct. 14, 2010

(65) Prior Publication Data
US 2012/0024707 A1    Feb. 2, 2012

(30) Foreign Application Priority Data

Apr. 10, 2009  (JP) ................................. 2009-096086

(51) Int. Cl.
*G01N 27/453* (2006.01)
(52) U.S. Cl.
USPC ..................... 204/603; 73/864.91; 73/864.81; 422/68.1; 422/82.01; 435/287.1; 220/324; 204/451
(58) Field of Classification Search
USPC ................. 204/600–605, 451–454; 73/864.01–864.23, 864.91; 220/324; 422/68.1, 82.01; 435/287.1; 215/200
See application file for complete search history.

(56) References Cited

U.S. PATENT DOCUMENTS

| | | | |
|---|---|---|---|
| 5,384,024 A * | 1/1995 | Moring et al. | 204/602 |
| 2003/0102221 A1 | 6/2003 | Ozawa et al. | |
| 2004/0112749 A1 | 6/2004 | Shibasaki et al. | |
| 2005/0012593 A1* | 1/2005 | Harrod et al. | 340/5.72 |
| 2005/0097849 A1* | 5/2005 | Hayes | 52/698 |
| 2005/0178462 A1* | 8/2005 | Py | 141/2 |
| 2006/0192108 A1* | 8/2006 | Yeatman et al. | 250/288 |
| 2008/0296160 A1* | 12/2008 | Ooura et al. | 204/601 |
| 2009/0020429 A1 | 1/2009 | Ozawa et al. | |

FOREIGN PATENT DOCUMENTS

| | | | |
|---|---|---|---|
| JP | 2003-166976 A | | 6/2003 |
| JP | 2008-298659 A | | 12/2008 |
| JP | 2009-042226 A | | 2/2009 |
| WO | WO 92/00461 | * | 1/1992 |
| WO | WO 02/079773 A1 | | 10/2002 |

* cited by examiner

*Primary Examiner* — Jennifer Dieterle
(74) *Attorney, Agent, or Firm* — McDermott Will & Emery LLP (57) ABSTRACT

The solution reservoir apparatus of the capillary electrophoresis apparatus securely affixes an evaporation-preventing membrane to a container when a capillary is inserted or withdrawn, without extending the cathode end of the capillary. The solution reservoir apparatus comprises a container for reserving a sample or solution, a cover having a bore through which the capillary is passed and covering the container, an evaporation-preventing membrane having a capillary hole through which the capillary is passed, and a container holder for holding the container. The evaporation-preventing membrane has a projection provided at the periphery of the capillary hole, the projection of the evaporation-preventing membrane is engaged with the bore on the cover when the evaporation-preventing membrane is positioned on the cover, and the evaporation-preventing membrane is supported by the cover.

24 Claims, 10 Drawing Sheets

CAPILLARY ELECTROPHORESIS APPARATUS

RELATED APPLICATIONS

This application is the U.S. National Phase under 35 U.S.C. §371 of International Application No. PCT/JP2010/056357, filed on Apr. 8, 2010, which in turn claims the benefit of Japanese Application No. 2009-096086, filed on Apr. 10, 2009, the disclosures of which Applications are incorporated by reference herein.

TECHNICAL FIELD

The present invention relates to a capillary electrophoresis apparatus that separates and analyzes a sample, such as DNA or a protein, via electrophoresis. More particularly, the present invention relates to a solution reservoir apparatus that reserves a solution, such as a sample solution, buffer solution, reagent solution, or washing solution.

BACKGROUND ART

A solution, such as a sample, reagent, buffer, or washing solution, used for a capillary electrophoresis apparatus is reserved in a container hermetically sealed with an evaporation-preventing membrane. Capillaries are brought into contact with a solution in a container through bores provided on an evaporation-preventing membrane.

An evaporation-preventing membrane is made of an elastic material. When capillaries are passing through bores on an evaporation-preventing membrane, the bores are contracted due to the elastic force, and the evaporation-preventing membrane hermetically seals the capillary peripheries. When capillaries are passed through bores on the evaporation-preventing membrane, a driving force that forces the capillaries into the bores against the friction between the capillaries and bores is necessary. When capillaries are withdrawn from bores on the evaporation-preventing membrane, a driving force that withdraws the capillaries against the friction is necessary. When capillaries are withdrawn from bores on the evaporation-preventing membrane, the evaporation-preventing membrane is raised up apart from the container due to the friction between capillaries and bores. When such friction is strong, not only the evaporation-preventing membrane but also the container may be raised up.

In order to overcome such drawbackes, the capillary electrophoresis apparatus described in WO 2002/079773 (A1) involves the use of a stripper. By pressing down the evaporation-preventing membrane with a stripper, the evaporation-preventing membrane or container is prevented from being raised when withdrawing capillaries from the evaporation-preventing membrane.

Engagement sections are provided in the capillary electrophoresis apparatus described in JP Patent (Kokai) No. 2008-298659 A so as to prevent the evaporation-preventing membrane from being detached from various sample-containing containers, such as buffer containers, or to prevent a container from being detached from the container holder, even when capillaries are inserted or withdrawn.

DISCLOSURE OF THE INVENTION

Object to be Attained by the Invention

The present inventors conducted concentrated studies on the solution reservoir apparatus of the capillary electrophoresis apparatus and consequently attained the finding described below. In the capillary electrophoresis apparatus disclosed in WO 2002/079773 (A1), a stripper is provided between a septum and a load header. Accordingly, it is necessary to maintain sufficient space for a stripper, and the cathode ends of the capillaries must be extended so that they may be soaked in the solution.

The capillary electrophoresis apparatus disclosed in JP Patent (Kokai) No. 2008-298659 A holds an evaporation-preventing membrane with an outer edge of the container. Accordingly, a sufficient distance should be maintained between the evaporation-preventing membrane and the solution, and the cathode ends of the capillaries must be extended to maintain such distance.

If the cathode ends of the capillaries are extended, the area of the cathode end that comes into contact with air is increased, temperature differences between cathode ends are increased, and variations in the measurement results among capillaries may be increased.

Accordingly, it is an object of the present invention to securely hold an evaporation-preventing membrane on the container of a solution reservoir apparatus of a capillary electrophoresis apparatus when inserting and withdrawing a capillary without extending the cathode end of the capillary.

Means for Attaining the Object

The present invention relates to a solution reservoir apparatus of a capillary electrophoresis apparatus. In the present invention, an evaporation-preventing membrane having a capillary hole through which a capillary is passed has a projection formed at the periphery of the capillary hole. When the evaporation-preventing membrane is provided on a cover, a projection of the evaporation-preventing membrane is engaged with the bore on the cover, and the evaporation-preventing membrane is thus supported by the cover.

EFFECTS OF THE INVENTION

According to the present invention, the evaporation-preventing membrane can remain securely affixed to a container when inserting a capillary into or withdrawing a capillary from the solution reservoir apparatus of a capillary electrophoresis apparatus without extending the cathode end of the capillary.

DESCRIPTION OF NUMERAL REFERENCES

101: capillary; 102: load header; 103: pump mechanism; 104: optical unit; 105: high-voltage power supply; 106: oven; 107: autosampler; 108: syringe; 109: block; 110: check valve; 111: polymer container; 112: anode buffer container; 113: anode electrode; 114: cathode electrode; 115: temperature control panel; 116: capillary head; 117: the cathode end of the capillary; 200: container; 201: reservoir section; 202: fastener member; 203: projection; 205: upper edge; 210: container holder; 211: hook; 220: evaporation-preventing membrane; 221: capillary hole; 222: projection; 230: cover; 231: bore; 232: edge; 250: seal member; 301: solution; 2221: cylindrical section; 2222: bottom; 2223: end bore; 2224: protruding portion

EMBODIMENTS FOR CARRYING OUT THE INVENTION

Figure 1:
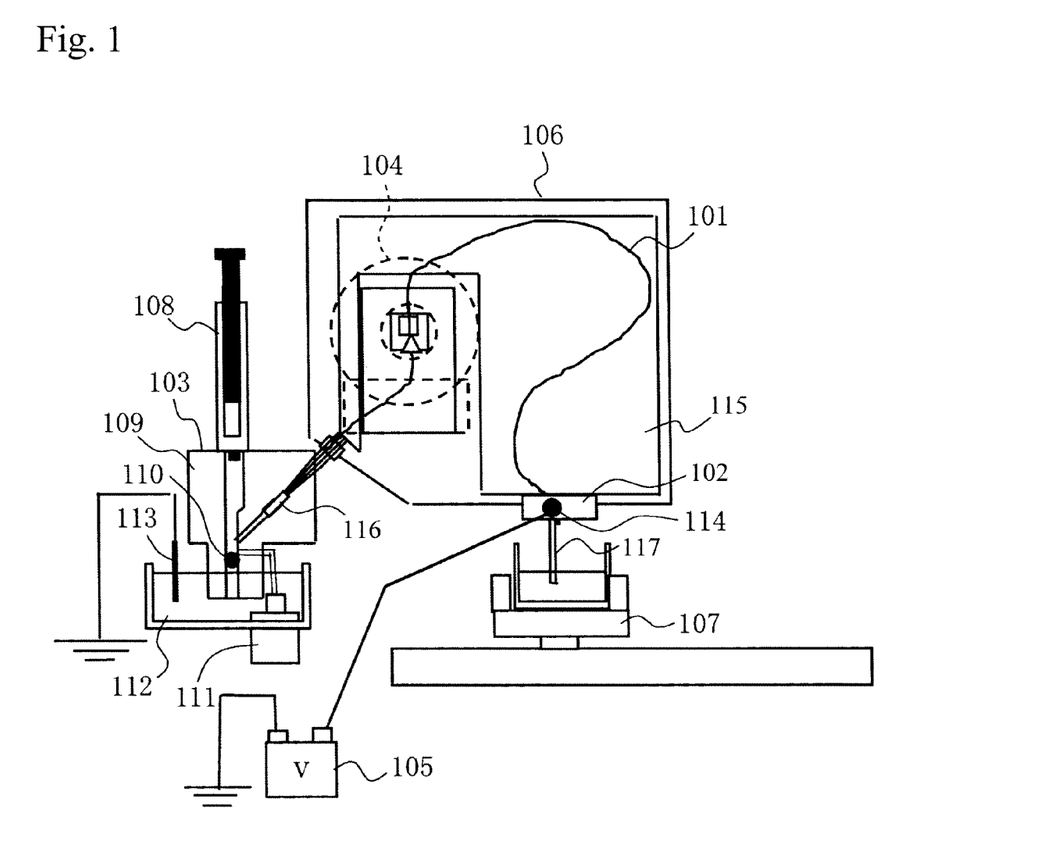
FIG. 1 schematically shows a capillary electrophoresis apparatus.

FIG. 1 schematically shows a capillary electrophoresis apparatus according to an embodiment. The capillary electrophoresis apparatus according to this embodiment comprises a capillary array comprising a single capillary or a plurality of capillaries 101, a pump mechanism 103 for injecting the capillary 101 into a polymer, an optical unit 104 for irradiating a sample in the capillary 101 with light and detecting fluorescence emitted from the sample, a high-voltage power supply 105 for applying a high voltage to the capillary 101, an oven 106 for maintaining the capillary 101 at constant temperature, and an autosampler 107 for transporting a container containing a sample, a solution, or the like.

The capillary 101 is a replaceable member, and it is replaced when measurement techniques are changed or it becomes damaged or deteriorated. The capillary 101 is composed of a glass tube having an inner diameter of a few tens to a few hundred micrometers and an outer diameter of a few hundred micrometers, and the surface thereof is coated with polyimide. The capillary 101 is filled with a separation medium for imparting differences in migration velocity at the time of electrophoresis. There are fluidic and non-fluidic separation media, and a fluidic polymer is used in this embodiment.

The capillary head 116 is provided at one end of the capillary 101, and the cathode end of the capillary 117 is provided at the other end. The capillary head 116 is composed of a bundle of ends of the capillaries 101 and has a function to connect the pump mechanism 103 to the capillaries 101. The cathode end of the capillary 117 is brought into contact with a sample, a solution, or the like. The capillary 101 is fixed to a load header 102 at the cathode end of the capillary. A cathode electrode 114 is provided on the load header 102.

The optical unit 104 is composed of an irradiation unit and a detection unit. The optical unit 104 has the function of irradiating a portion in which a polyimide coating of the capillary 101 has been removed (i.e., a detection section) with an excitation light. The detection unit has the function of detecting fluorescence emitted from a sample inside the detection area of the capillary 101. The sample is analyzed on the basis of the light detected by the detection unit.

The pump mechanism 103 comprises a syringe 108, a block 109, a check valve 110, a polymer container 111, and an anode buffer container 112. By connecting the capillary head 116 to the block 109, the capillary 101 is connected to the flow channel inside the block 109. Through the operation of the syringe 108, a polymer in the polymer container 111 is transported through the flow channel in the block 109 to the capillary 101, so that the capillary 101 is filled with polymer or the polymer in the capillary 101 is replaced. The polymer in the capillary 101 is replaced after every measurement in order to improve measurement performance.

The anode buffer container 112 comprises an anode electrode 113 disposed therein. The high-voltage power supply 105 applies a high voltage between the anode electrode 113 and the cathode electrode 114.

The oven 106 holds the capillary array 102 in flat shape between the temperature control panels 115 equipped with an insulator and a heater in order to maintain the capillary at constant temperature. A feedback temperature sensor is mounted on the temperature control panel. In addition, the load header 102 of the capillary array may be fixed on the oven to fix the tip of the capillary head 116 at a desirable position.

The autosampler 107 comprises three electric motors and linear guides for moving a transport stage and it is capable of moving the transport stage along three axes, namely upwardly or downwardly, rightwardly or leftwardly, and forwardly or backwardly. The transport stage is capable of transporting a buffer container, a washing container, a waste container, and a sample plate to the cathode end of the capillary 117 (i.e., the capillary electrode), according to need.

Figure 2A:
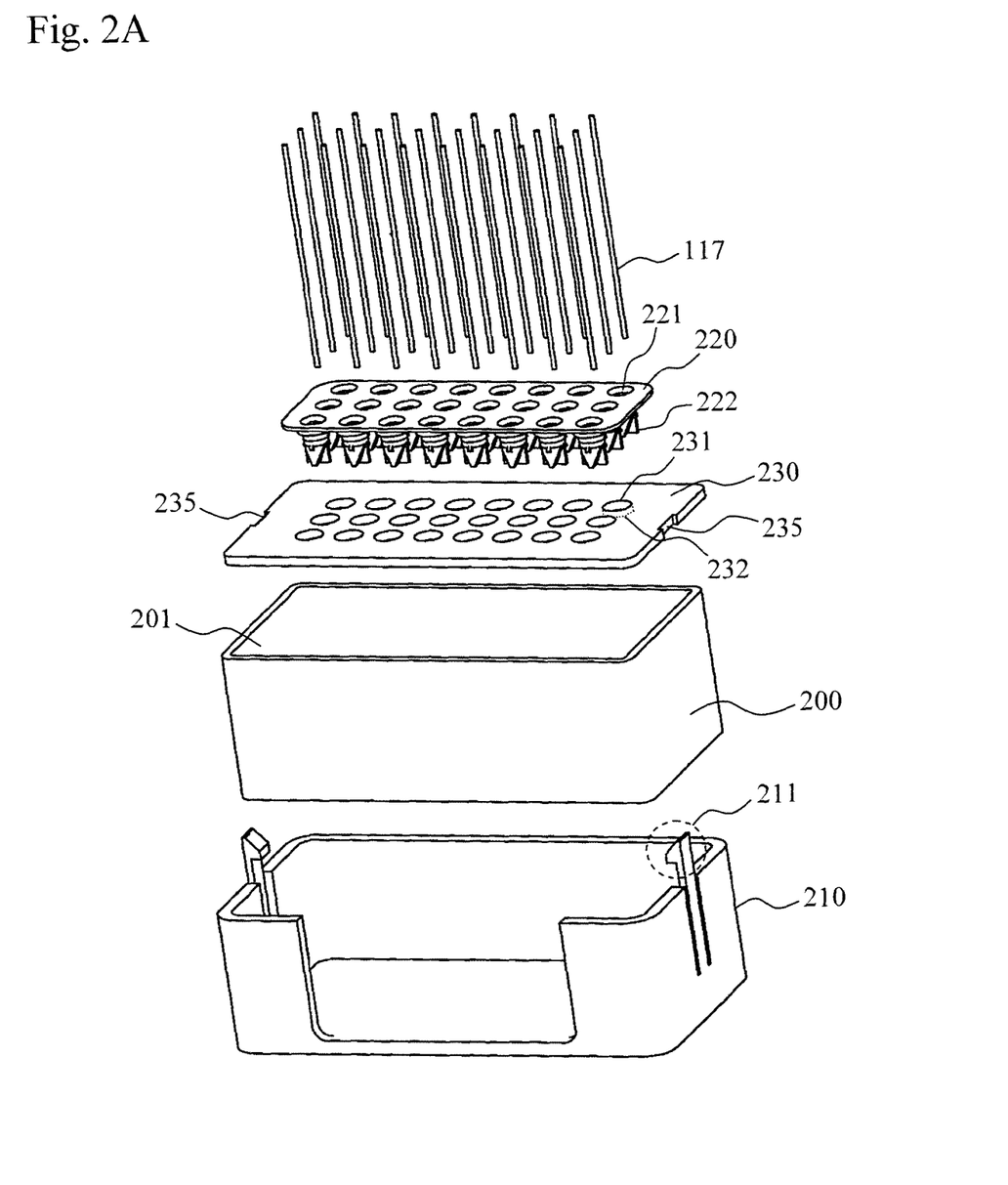
FIG. 2A is an exploded perspective view of the solution reservoir apparatus of the capillary electrophoresis apparatus according to the first embodiment.

The solution reservoir apparatus used for the capillary electrophoresis apparatus according to first embodiment is described with reference to FIGS. 2A, 2B, and 2C. As shown in FIG. 2A, the solution reservoir apparatus of this embodiment comprises a container 200, a container holder 210, an evaporation-preventing membrane 220, and a cover 230.

The container 200 comprises a reservoir section 201 that reserves a solution, such as a sample solution, buffer solution, reagent solution, or washing solution. According to this embodiment, the container 200 is adhered to the cover 230 with the use of an adhesive or via ultrasonic fusion bonding. The hooks 211 are provided on both sides of the container holder 210. A plurality of bores 231 are provided on the cover 230. Notches 235 are provided on both sides of the cover 230.

The evaporation-preventing membrane 220 comprises the capillary holes 221 through which the cathode ends of the capillaries 117 are passed and the projections 222. The projections 222 project from the lower surface of the evaporation-preventing membrane 220 so as to surround the capillary holes 221. The capillary holes 221 and the projections 222 are provided such that they correspond to the bores 231 on the cover 230. The edges 232 of the bores 231 on the lower surface of the cover 230 and the projections 222 on the evaporation-preventing membrane 220 constitute an engagement section (described below). The evaporation-preventing membrane 220 is made of an elastic material, such as rubber or resin.

Figure 2B:
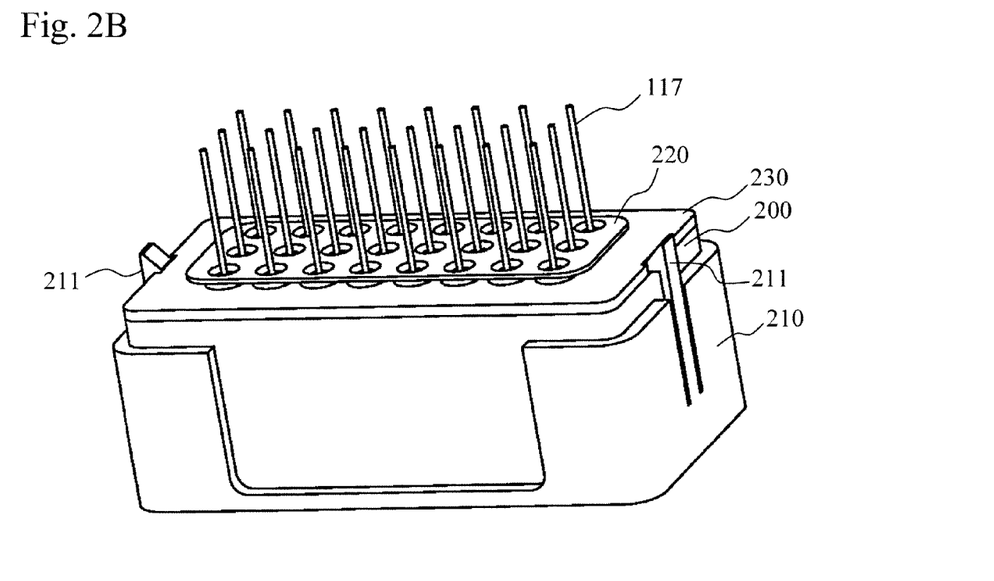
FIG. 2B is an assembly view of the solution reservoir apparatus of the capillary electrophoresis apparatus according to the first embodiment.

FIG. 2B shows the solution reservoir apparatus of this embodiment in an assembled state. The container holder 210 holds the container 200. The hooks 211 of the container holder 210 are engaged with the edges on the upper surface of the container 200. Thus, the containers 200 are fixed in the container holder 210.

The upper surface of the container 200 is covered with the cover 230, and the evaporation-preventing membrane 220 is mounted on the upper surface of the cover 230. According to the embodiment shown in FIG. 2B, a single container 200 is held in the container holder 210, although a plurality of containers 200 may be arranged and held therein.

Figure 2C:
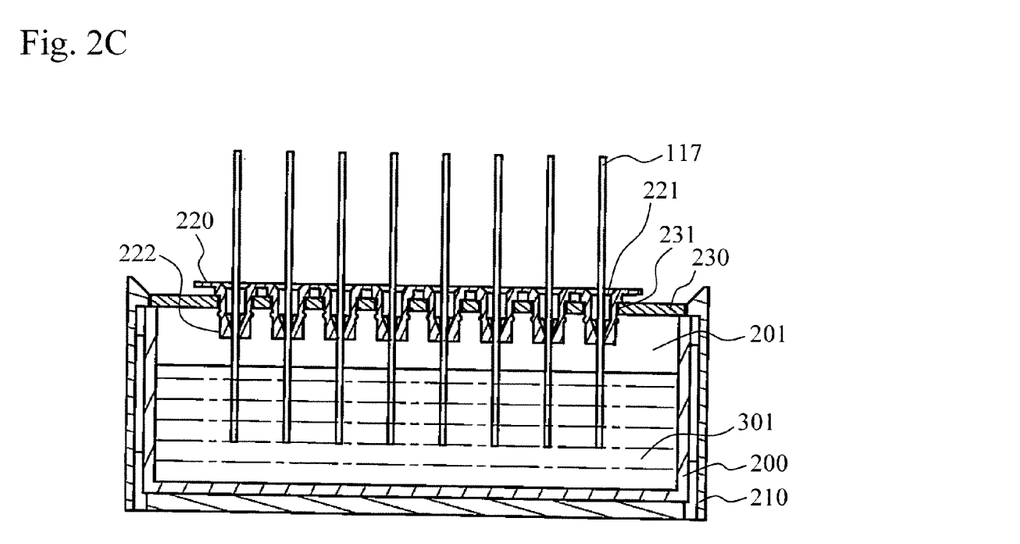
FIG. 2C is a cross-sectional view of the solution reservoir apparatus of the capillary electrophoresis apparatus according to the first embodiment.

FIG. 2C shows the solution reservoir apparatus of this embodiment which is in use. As shown in FIG. 2C, the container 200 is mounted in the container holder 210, and a solution 301, such as a buffer solution, reagent solution, washing solution, or washing waste is reserved in the reservoir section 201 of the container 200. The projections 222 of the evaporation-preventing membrane 220 are engaged with the bores 231 of the cover 230. The cathode ends of the capillaries 117 are passed through the capillary holes 221 of the evaporation-preventing membrane 220.

Figure 3A:
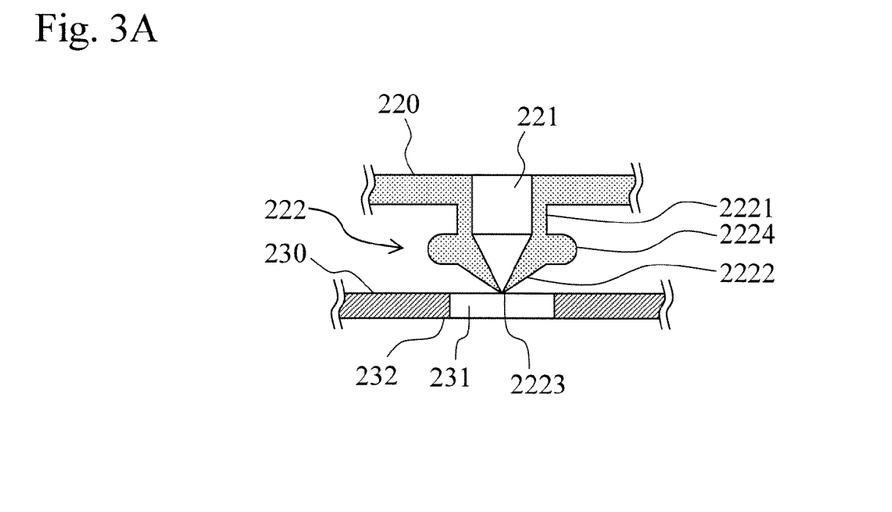
FIG. 3A is a view showing a constitutional example of a capillary hole and a projection of the evaporation-preventing membrane of the solution reservoir apparatus of the capillary electrophoresis apparatus.
Figure 3B:
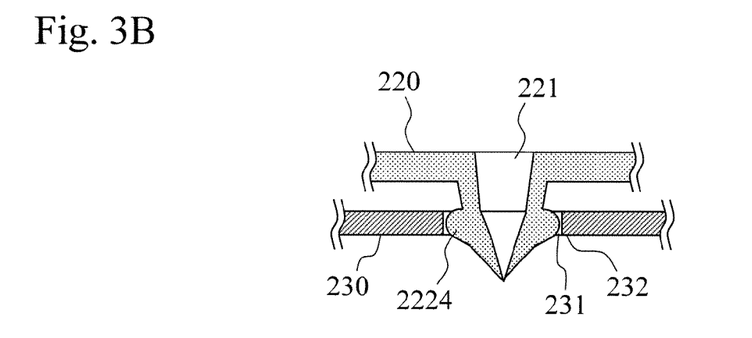
FIG. 3B is a view showing a constitutional example of a capillary hole and a projection of the evaporation-preventing membrane of the solution reservoir apparatus of the capillary electrophoresis apparatus.
Figure 3C:
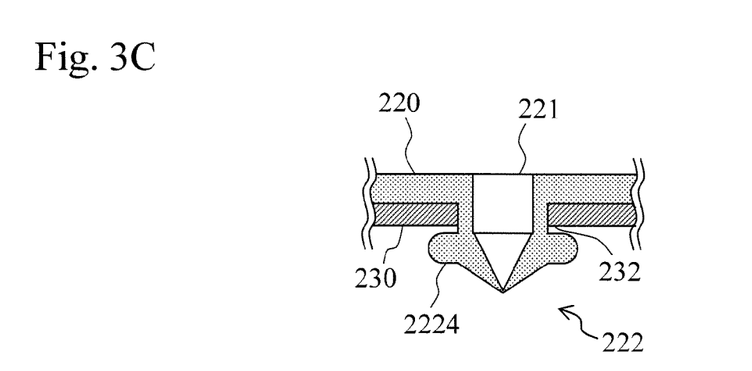
FIG. 3C is a view showing a constitutional example of a capillary hole and a projection of the evaporation-preventing membrane of the solution reservoir apparatus of the capillary electrophoresis apparatus.

The constitutions of the capillary holes 221 and the projections 222 of the evaporation-preventing membrane 220 are described with reference to FIGS. 3A, 3B, and 3C. As shown in FIG. 3A, the projections 222 are provided on the lower surface of the evaporation-preventing membrane 220 so as to surround the capillary holes 221. The projections 222 each have a cylindrical section 2221, a protruding portion 2224 provided at the outer periphery of the cylindrical section 2221, a conical bottom 2222 connected to the tip of the cylindrical section 2221, and an end bore 2223 provided at the lower end of the bottom.

The cross-sectional shape of the protruding portion 2224 of the projection 222 is preferably circular, but it may be rectangular. The protruding portion 2224 is undercut in a draft direction at the time of molding for the convenience of production. Thus, the protruding portion is withdrawn with the utilization of elastic body deformation.

A capillary hole 221 reaches the inside of the cylindrical section 2221. The inner surface of the capillary hole 221 is tapered and the inner diameter is reduced at the bottom 2222. The capillary hole 221 is connected to the end bore 2223.

The outer diameter of the cylindrical section 2221 of the projection 222 is equal to or slightly less than the inner diameter of a bore 231 on the cover 230. The outer diameter of the protruding portion 2224 is slightly greater than the inner diameter of a bore 231 on the cover 230. As shown in FIG. 3B, accordingly, the cylindrical section 2221 of the projection 222 should be elastically deformed to the extent that the protruding portion 2224 can be inserted into a bore 231 on the cover 230, when inserting the projection 222 of the evaporation-preventing membrane 220 into a bore 231 on the cover 230. When the protruding portion 2224 of the projection 222 of the evaporation-preventing membrane 220 has been passed through a bore 231 on the cover 230, the shape of the cylindrical section 2221 of the projection 222 is returned to the original state, and the protruding portion 2224 projects from a bore 231 on the cover 230, as shown in FIG. 3C. When the projection 222 of the evaporation-preventing membrane 220 is inserted into a bore 231 on the cover 230, the protruding portion 2224 of the projection 222 abuts the edge 232 of a bore 231 on the cover 230, as shown in FIG. 3C. Accordingly, the evaporation-preventing membrane 220 cannot be detached from the cover 230. Unless the projection 222 of the evaporation-preventing membrane 220 is deformed with special force, specifically, the projection 222 cannot be removed from a bore 231 on the cover 230. According to this embodiment, the protruding portion 2224 of the projection 222 of the evaporation-preventing membrane 220 and the edge 232 of the bore 231 on the cover 230 constitute the engagement section between the evaporation-preventing membrane 220 and the cover 230.

While the inner diameter of the capillary hole 221 is greater than the outer diameter of the cathode end of the capillary 117, the inner diameter of the end bore 2223 is slightly less than the outer diameter of the cathode end of the capillary 117. When the cathode end of the capillary 117 is inserted into the capillary hole 221 of the evaporation-preventing membrane 220 and is passed through the end bore 2223 of the projection 222 of the evaporation-preventing membrane 220, the periphery of the cathode end of the capillary 117 is contracted due to the elastic force of the end bore 2223. That is, no gap is generated between the cathode end of the capillary 117 and the end bore 2223. Accordingly, the solution evaporated from the reservoir section 201 would not leak from the periphery of the cathode end of the capillary 117. Specifically, the reservoir section 201 of the container 200 is completely hermetically sealed.

When the cathode end of the capillary 117 is not inserted into the capillary hole 221 of the evaporation-preventing membrane 220, the end bore 2223 of the projection 222 of the evaporation-preventing membrane 220 is contracted due to the elastic force, and it remains closed. When the cathode end of the capillary 117 is not inserted, accordingly, the reservoir section 201 of the container 200 is completely hermetically sealed.

If the shape of the projection 222 is not returned to the original state after the projection 222 of the evaporation-preventing membrane 220 is inserted into a bore 231 on the cover 230, the evaporation-preventing membrane 220 cannot be held by the cover 230. It is thus preferable that the evaporation-preventing membrane 220 be made of a transparent or semi-transparent elastic material in order to visually inspect the deformation state of the projection 222. From the viewpoint of drug resistance or other properties, transparent silicone rubber is preferable as a material for the evaporation-preventing membrane 220. The container 200 and the cover 230 may also be made of transparent materials. Thus, the deformation state of the projection 222 can be observed from the outside.

Figure 4A:
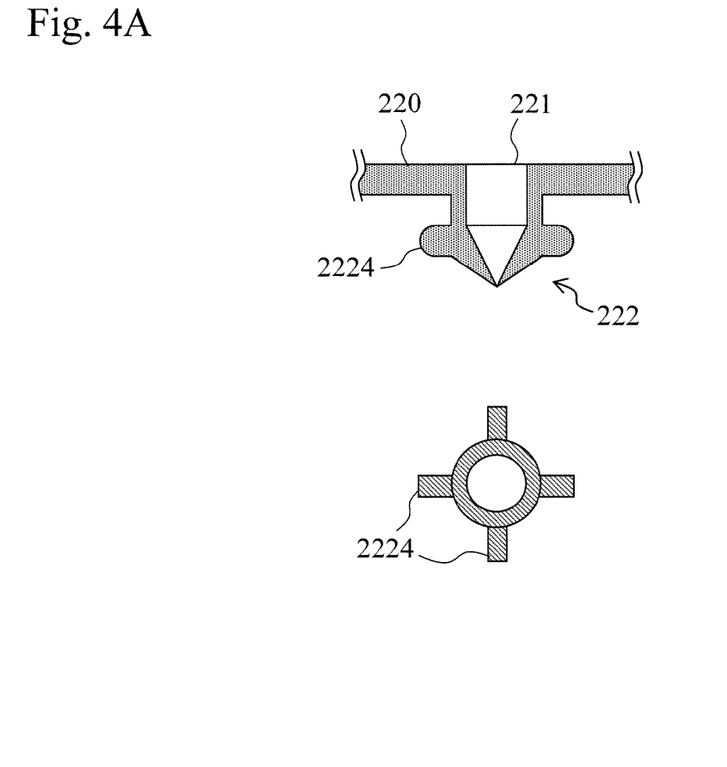
FIG. 4A is a view showing a constitutional example of the protruding portions of the projection of the evaporation-preventing membrane of the solution reservoir apparatus of the capillary electrophoresis apparatus.
Figure 4B:
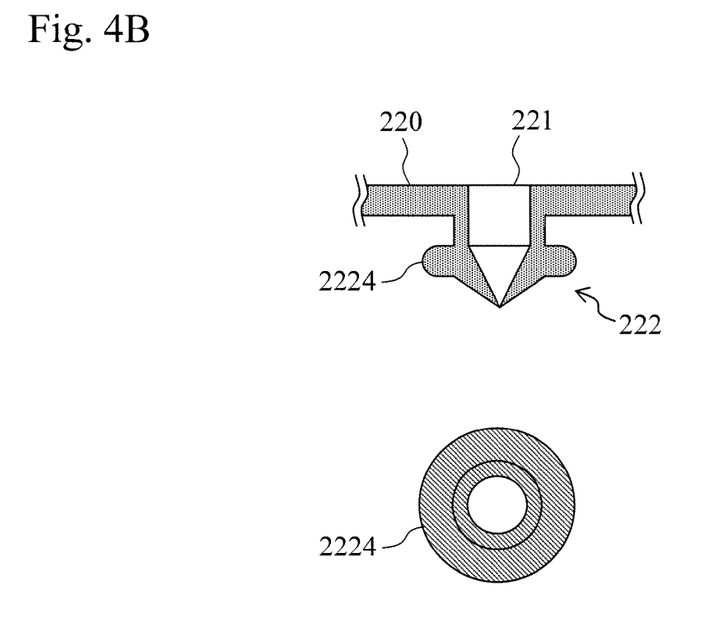
FIG. 4B is a view showing a constitutional example of the protruding portions of the projection of the evaporation-preventing membrane of the solution reservoir apparatus of the capillary electrophoresis apparatus.

FIG. 4A and FIG. 4B each show an embodiment of the protruding portion 2224 of the projection 222 of the evaporation-preventing membrane 220. As shown in FIG. 4A, the protruding portion 2224 may be constituted by a plurality of projections extending radially outwardly. Alternatively, the protruding portion 2224 may be constituted by a band- or doughnut-shaped projection extending along the circumference, as shown in FIG. 4B.

Functions of the projection 222 of the evaporation-preventing membrane 220 in the solution reservoir apparatus of this embodiment are described next. When the cathode end of the capillary 117 is inserted into the capillary hole 221 of the evaporation-preventing membrane 220, the cathode end of the capillaries 117 is forced to move downwardly and in a direction vertical to the evaporation-preventing membrane 220 and the cover 230. Friction occurs between the cathode end of the capillary 117 and the end bore 2223 of the projection 222 of the evaporation-preventing membrane 220. This friction force acts to prevent the cathode end of the capillary 117 from being inserted into the capillary hole and to press the evaporation-preventing membrane 220 downwardly. The evaporation-preventing membrane 220 is pressed against the cover 230 by such downward force. However, the evaporation-preventing membrane 220 is supported by the cover 230 and it thus does not move downwardly.

When the cathode end of the capillary 117 is withdrawn from the capillary hole 221 of the evaporation-preventing membrane 220, the cathode end of the capillary 117 is also forced to move upwardly and in a direction vertical to the evaporation-preventing membrane 220 and the cover 230. Friction occurs between the cathode end of the capillary 117 and the end bore 2223 of the projection 222 of the evaporation-preventing membrane 220. This friction force acts to prevent the cathode end of the capillary 117 from being withdrawn from the capillary hole and to press the evaporation-preventing membrane 220 upwardly. The evaporation-preventing membrane 220 is raised and detached from the cover 230 by such upward force. However, the protruding portion 2224 of the projection 222 of the evaporation-preventing membrane 220 is engaged with the edge 232 of a bore 231 on the cover 230. Thus, the evaporation-preventing membrane 220 cannot further depart from the cover 230.

In the case of the solution reservoir apparatus of the capillary electrophoresis apparatus according to this embodiment, the outer diameter of the cathode end of the capillary 117 is less than the inner diameter of the end bore 2223 of the projection 222 of the evaporation-preventing membrane 220, although it is greater than the inner diameter of the capillary hole 221. When the cathode end of the capillary 117 is withdrawn or inserted, accordingly, friction that acts on the cathode end of the capillary 117 selectively occurs between the cathode end of the capillary 117 and the end bore 2223 of the projection 222 of the evaporation-preventing membrane 220, and such friction is relatively small. Accordingly, the cathode end of the capillary 117 can be withdrawn or inserted with little force.

According to this embodiment, engagement between the protruding portion 2224 of the projection 222 of the evaporation-preventing membrane 220 and the edge 232 of a bore 231 on the cover 230 can prevent excessive deformation of the evaporation-preventing membrane 220. Thus, the thickness of the evaporation-preventing membrane 220 can be reduced. Further, the evaporation-preventing membrane 220 can be made of a relatively soft material. By constituting the evaporation-preventing membrane 220 with a relatively soft elastic material, friction that occurs when withdrawing or inserting the cathode ends of the capillaries can be reduced.

Figure 5A:
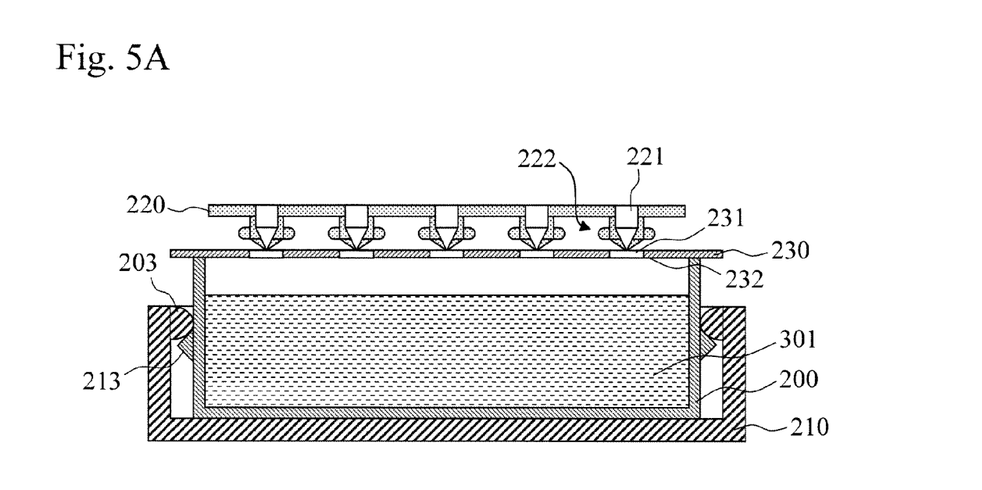
FIG. 5A is an exploded view of the solution reservoir apparatus of the capillary electrophoresis apparatus according to the second embodiment.
Figure 5B:
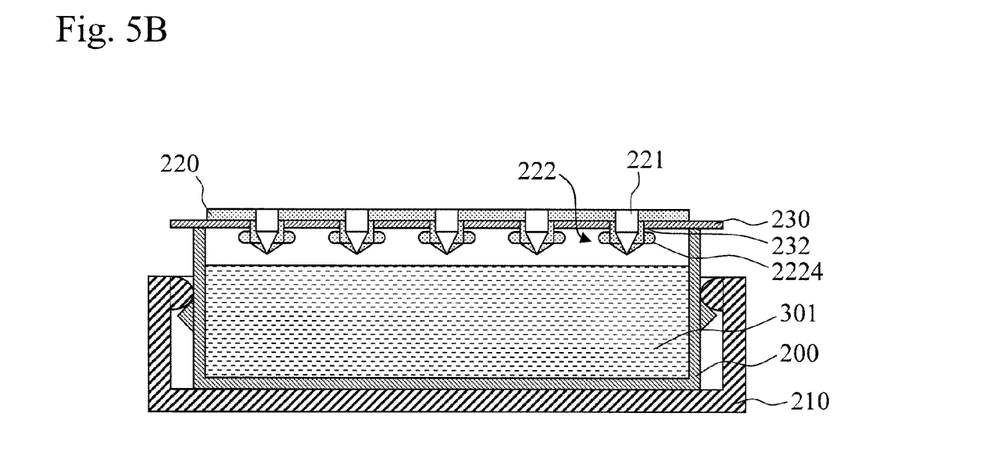
FIG. 5B is an assembly view of the solution reservoir apparatus of the capillary electrophoresis apparatus according to the second embodiment.

The solution reservoir apparatus used for the capillary electrophoresis apparatus according to the second embodiment is described with reference to FIGS. 5A and 5B. As shown in FIG. 5A, the solution reservoir apparatus of this embodiment comprises a container 200, a container holder 210, an evaporation-preventing membrane 220, and a cover 230. The projections 203 provided on the outer surface of the container 200 are engaged with the projections 213 provided on the inner surface of the container holder 210. Thus, the container 200 is fixed in the container holder 210.

The container 200 is adhered to the cover 230 with the use of an adhesive or via ultrasonic fusion bonding. A plurality of bores 231 are provided on the cover 230.

The evaporation-preventing membrane 220 comprises the capillary holes 221 through which the cathode ends of the capillaries 117 are passed and the projections 222. The constitutions of the capillary holes 221 and the projections 222 were described with reference to FIGS. 3A, 3B, 3C, 4A, and 4B above. In this embodiment, the protruding portion 2224 of the projection 222 of the evaporation-preventing membrane 220 and the edge 232 of the bore 231 on the cover 230 constitute the engagement section between the evaporation-preventing membrane 220 and the cover 230. FIG. 5B shows the condition in which the evaporation-preventing membrane 220 is mounted on the upper surface of the cover 230.

Figure 6A:
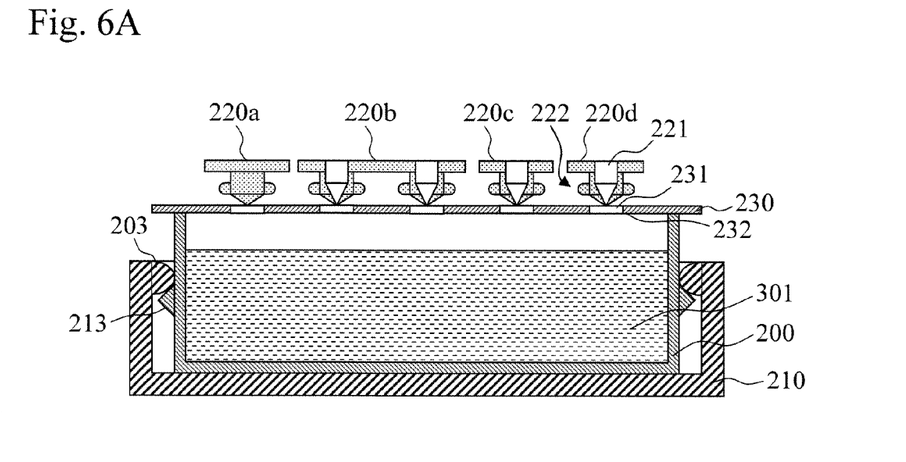
FIG. 6A is an exploded view of the solution reservoir apparatus of the capillary electrophoresis apparatus according to the third embodiment.
Figure 6B:
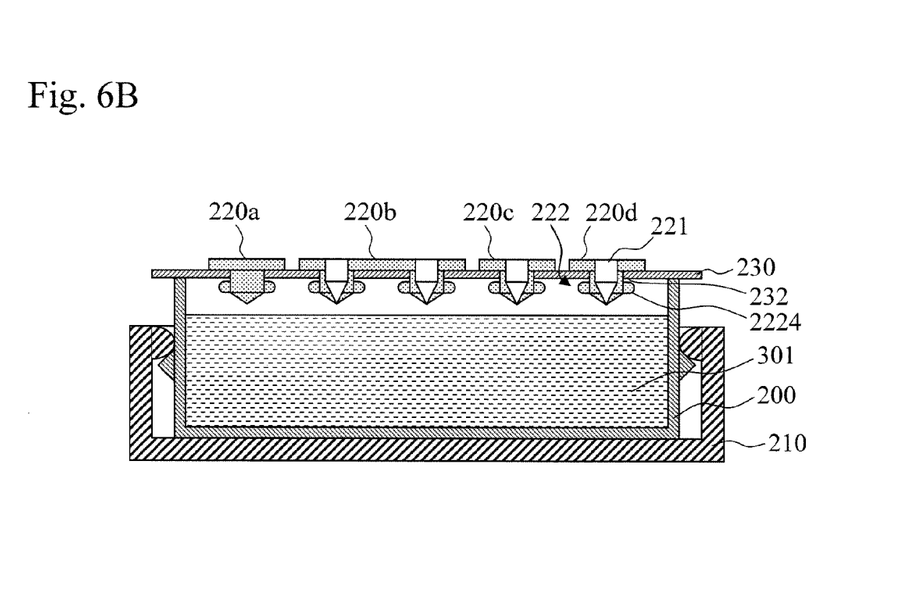
FIG. 6B is an assembly view of the solution reservoir apparatus of the capillary electrophoresis apparatus according to the third embodiment.

The solution reservoir apparatus used for the capillary electrophoresis apparatus of the third embodiment is described with reference to FIGS. 6A and 6B. As shown in FIG. 6A, the solution reservoir apparatus of this embodiment comprises a container 200, a container holder 210, a plurality of evaporation-preventing membranes 220a to 200d, and a cover 230. The projections 203 provided on the outer surface of the container 200 are engaged with the projections 213 provided on the inner surface of the container holder 210. Thus, the container 200 is fixed in the container holder 210. The container 200 is adhered to the cover 230 with the use of an adhesive or via ultrasonic fusion bonding. A plurality of bores 231 are provided on the cover 230.

The solution reservoir apparatus according to this embodiment comprises a plurality of evaporation-preventing membranes 220a to 200d, and each evaporation-preventing membrane is equipped with at least one capillary hole 221 and projection 222. The evaporation-preventing membrane may be provided for each capillary. The constitutions of the capillary holes 221 and the projections 222 were described with reference to FIGS. 3A, 3B, 3C, 4A, and 4B above. In this embodiment, the protruding portion 2224 of the projection 222 of the evaporation-preventing membrane and the edge 232 of the bore 231 on the cover 230 constitute the engagement section between the evaporation-preventing membrane 220 and the cover 230. FIG. 5B shows a condition in which a plurality of evaporation-preventing membranes 220a to 200d are mounted on the upper surface of the cover 230.

Figure 7A:
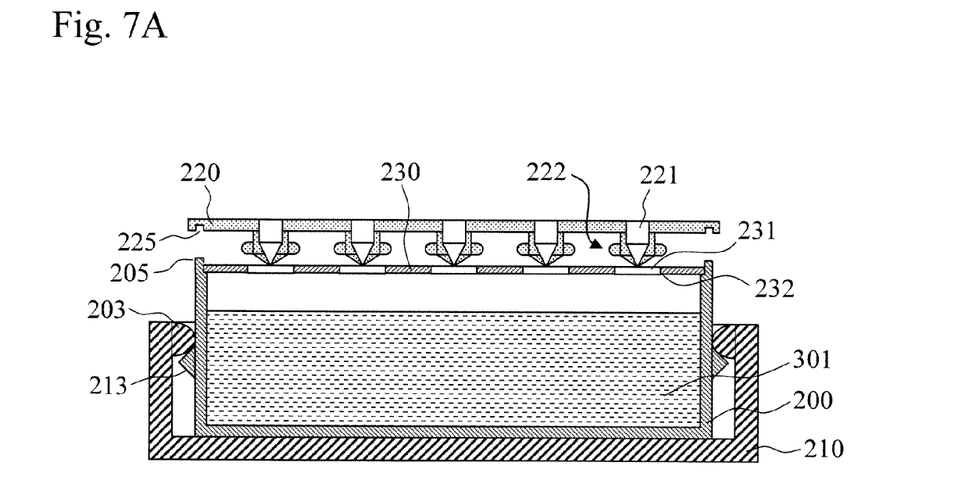
FIG. 7A is an exploded view of the solution reservoir apparatus of the capillary electrophoresis apparatus according to the fourth embodiment.
Figure 7B:
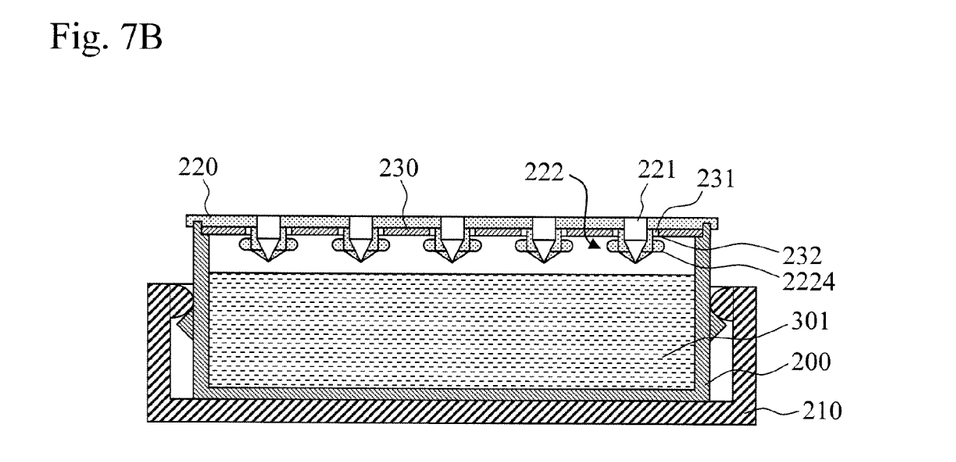
FIG. 7B is an assembly view of the solution reservoir apparatus of the capillary electrophoresis apparatus according to the fourth embodiment.

The solution reservoir apparatus used for the capillary electrophoresis apparatus of the fourth embodiment is described with reference to FIGS. 7A and 7B. As shown in FIG. 7A, the solution reservoir apparatus of this embodiment comprises a container 200, a container holder 210, an evaporation-preventing membrane 220, and a cover 230. The projections 203 provided on the outer surface of the container 200 are engaged with the projections 213 provided on the inner surface of the container holder 210. Thus, the container 200 is fixed in the container holder 210.

The evaporation-preventing membrane 220 comprises the capillary holes 221 through which the cathode ends of the capillaries are passed and the projections 222. The constitutions of the capillary holes 221 and the projections 222 were described with reference to FIGS. 3A, 3B, 3C, 4A, and 4B above. In this embodiment, the protruding portion 2224 of the projection 222 of the evaporation-preventing membrane 220 and the edge 232 of the bore 231 on the cover 230 constitute the engagement section between the evaporation-preventing membrane 220 and the cover 230.

The upper edge 205 of the container 200 projects upwardly from the cover 230 so as to surround the cover 230. A recess 225 is provided on the lower surface of the evaporation-preventing membrane 220. FIG. 7B shows a condition in which the evaporation-preventing membrane 220 is mounted. As shown in FIG. 7B, the upper edge 205 of the container 200 is engaged with the recess 225 of the evaporation-preventing membrane 220. According to this embodiment, the evaporation-preventing membrane 220 is fixed by the container 200.

When capillaries are withdrawn from the evaporation-preventing membrane of the solution reservoir apparatus of the capillary electrophoresis apparatus, the protruding portion 2224 of the projection 222 of the evaporation-preventing membrane is engaged with the edge 232 of a bore 231 on the cover 230. This can prevent the evaporation-preventing membrane from being detached from the container 200 with certainty. The engagement section constituted by the protruding portion 2224 of the projection 222 and the edge 232 of a bore 231 on the cover 230 is provided for each capillary. Accordingly, effects of preventing the evaporation-preventing membrane from being detached from the container 200 can be expected, regardless of the number of capillaries.

Since the evaporation-preventing membrane is positioned on the cover 230 of the solution reservoir apparatus, a downward force applied to the evaporation-preventing membrane when inserting capillaries is supported by the cover. Thus, it does not occure that the evaporation-preventing membrane is deformed to be brought into contact with a solution. Thus, thickness of the evaporation-preventing membrane can be reduced. Further, the dimensions of the cathode end of the capillary would not be increased. When the number of capillaries is increased, the area of the evaporation-preventing membrane is increased. Even if in such case, the evaporation-preventing membrane can be securely supported by the cover.

Figure 8A:
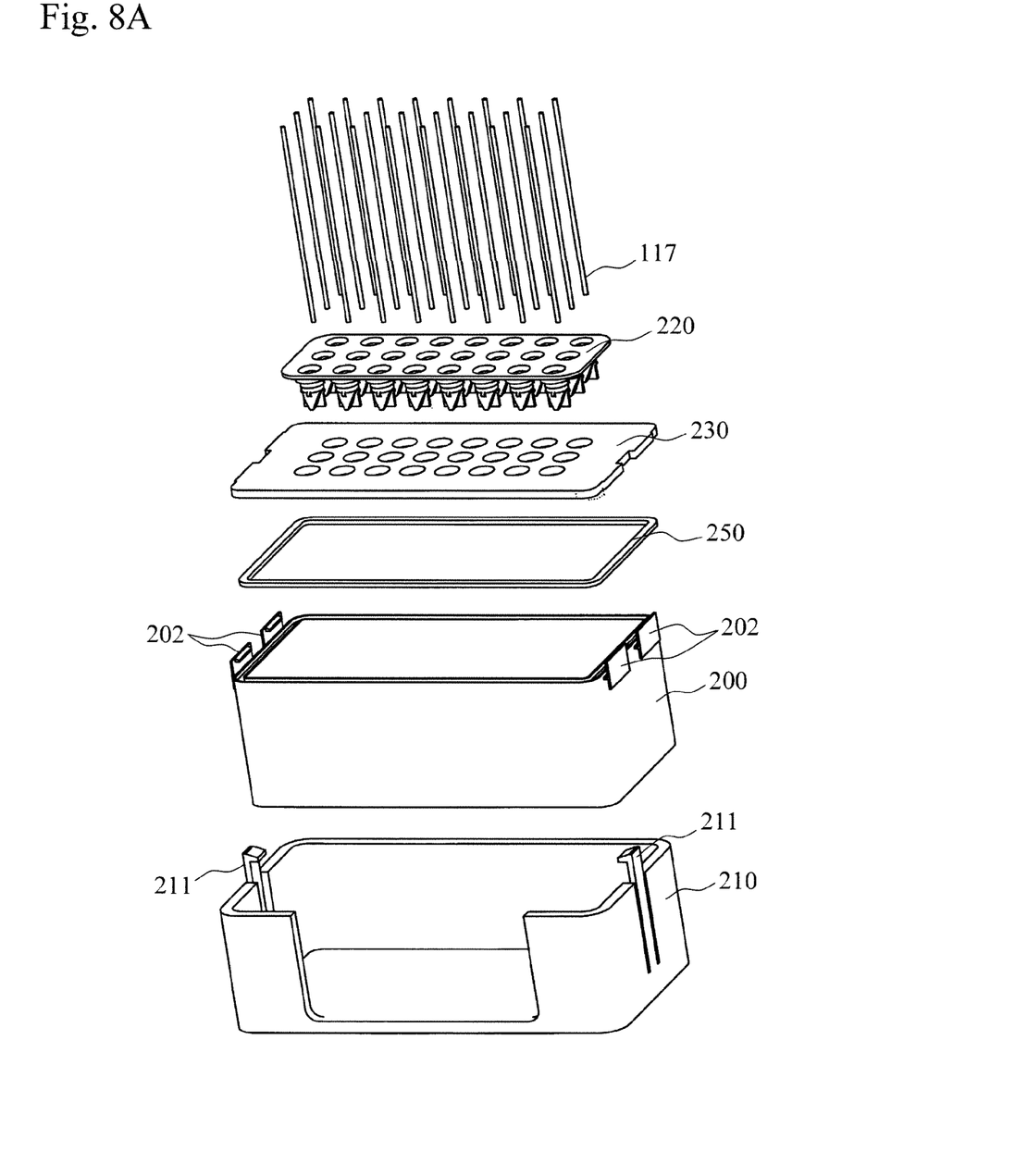
FIG. 8A is an exploded perspective view of the solution reservoir apparatus of the capillary electrophoresis apparatus according to the fifth embodiment.

The solution reservoir apparatus used for the capillary electrophoresis apparatus of the fifth embodiment is described with reference to FIGS. 8A, 8B, and 8C. As shown in FIG. 8A, the solution reservoir apparatus according to this embodiment comprises a container 200, a container holder 210, an evaporation-preventing membrane 220, a seal member 250, and a cover 230.

According to this embodiment, the cover 230 is detachably mounted on the container 200. Fastener members 202 are mounted on both sides of the container 200. The fastener members 202 may be snap-fit fastener devices utilizing the elastic deformation of resin. Such fastener devices are known for applications in fastening the covers of food containers, and such devices can be made in a variety of forms. A seal member 250 is inserted between the cover 230 and the container 200. The seal member 250 is a sealing member constituted by rubber, resin, or another material and it is utilized in a variety of fields in the form of a gasket, packing, or the like. A recess may be provided on the lower surface of the cover 230 with which the seal member 250 is to be engaged.

Figure 8B:
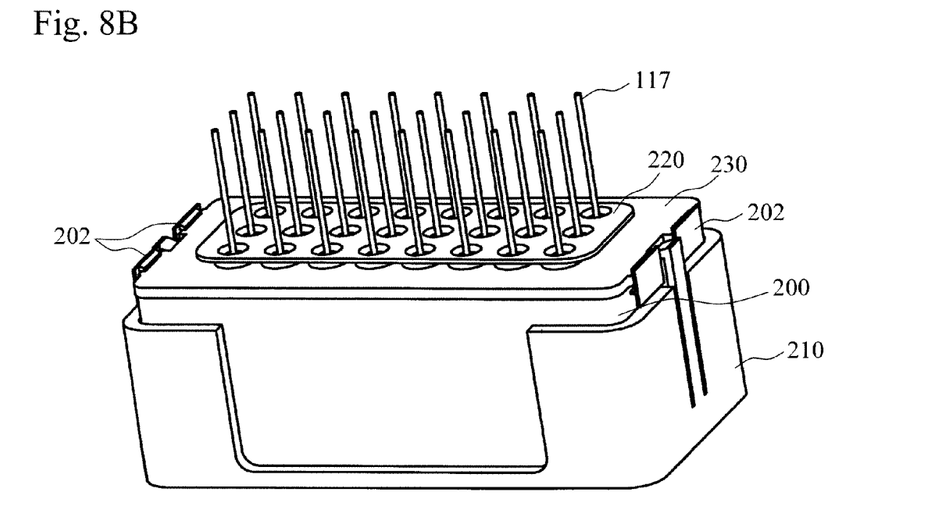
FIG. 8B is an assembly view of the solution reservoir apparatus of the capillary electrophoresis apparatus according to the fifth embodiment.

FIG. 8B shows the solution reservoir apparatus according to this embodiment in an assembled state. The container holder 210 holds the container 200. The hook 211 of the container holder 210 is engaged with the edge on the upper surface of the container 200. Thus, the container 200 is secured within the container holder 210.

Figure 8C:
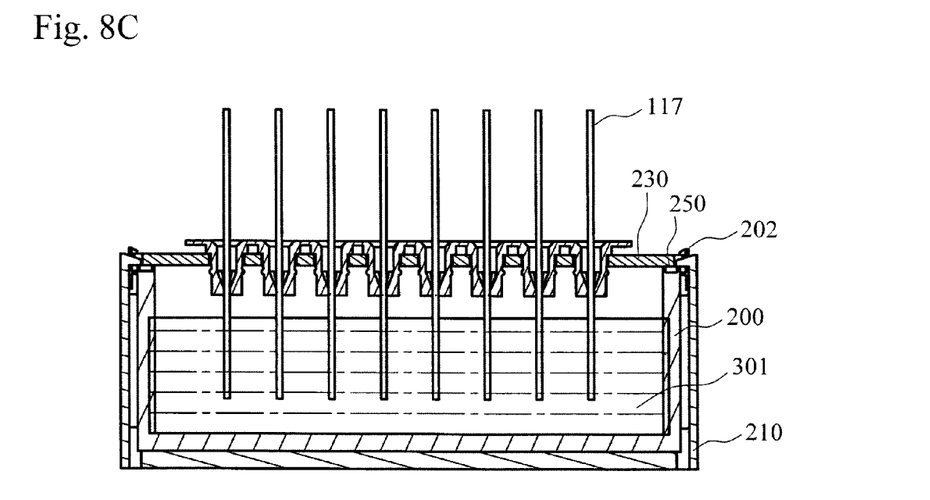
FIG. 8C is a cross-sectional view of the solution reservoir apparatus of the capillary electrophoresis apparatus according to the fifth embodiment.

FIG. 8C shows a condition in which the solution reservoir apparatus of this embodiment is used. As shown in FIG. 8C, the container 200 is mounted in the container holder 210, and the reservoir section 201 of the container 200 reserves a solution 301, such as a buffer solution, reagent solution, washing solution, or washing waste. The projection 222 of the evaporation-preventing membrane 220 is engaged with a bore 231 on the cover 230. The cathode end of the capillary 117 is passed through the capillary hole 221 of the evaporation-preventing membrane 220.

The present invention is not limited to the embodiments described above. A person skilled in the art would be readily able to understand that various modications can be made within the scope of the claimed inventions.

The invention claimed is:

1. A capillary electrophoresis apparatus comprising:
   at least one capillary,
   a power supply configured to apply voltage to both ends of the at least one capillary,
   an optical unit configured to irradiate a sample separated by electrophoresis in the at least one capillary with an excited light and configured to detect fluorescence emitted from the sample,
   a solution reservoir apparatus configured to reserve a sample or solution, and
   an autosampler configured to transport the solution reservoir apparatus,
   wherein the solution reservoir apparatus comprises:
      a container configured to reserve a sample or solution,
      a cover having a bore through which the at least one capillary is passed and configured to cover the container,
      an evaporation-preventing membrane configured for positioning on the cover, and
      a container holder configured to hold the container, wherein:
         the evaporation-preventing membrane comprises at least one projection configured for passing through the bore on the cover, said at least one projection comprises a capillary hole having a cylindrical section, an end bore, and at least two protruding portions provided at the outer periphery of the cylindrical section of the capillary hole, wherein the at least two protruding portions are configured for engaging with the bore on the cover when the evaporation-preventing membrane is positioned on the cover.

2. The capillary electrophoresis apparatus according to claim 1, wherein the at least two protruding portions comprise four protruding portions which are disposed radially on the outer periphery of the cylindrical section of the capillary hole.

3. The capillary electrophoresis apparatus according to claim 1, wherein outer diameters of the at least two protruding portions of the at least one projection are greater than an inner diameter of the bore on the cover.

4. The capillary electrophoresis apparatus according to claim 1, wherein an outer diameter of the cylindrical section of the at least one projection is less than or equal to an inner diameter of the bore on the cover.

5. The capillary electrophoresis apparatus according to claim 1, wherein an inner diameter of the end bore of the at least one projection is less than an outer diameter of the at least one capillary, and an inner diameter of the capillary hole of the evaporation-preventing membrane is greater than an outer diameter of the at least one capillary.

6. The capillary electrophoresis apparatus according to claim 1, wherein the at least one projection has a conical bottom that connects the cylindrical section to the end bore, and an inner surface of the capillary hole is tapered at a bottom.

7. The capillary electrophoresis apparatus according to claim 1, wherein the evaporation-preventing membrane comprises a plurality of evaporation-preventing membranes separated by a space and each of the plurality of evaporation-preventing membranes is equipped with at least one capillary hole and at least one projection.

8. The capillary electrophoresis apparatus according to claim 7, wherein each of the plurality of evaporation-preventing membranes is equipped with a single capillary hole and projection.

9. The capillary electrophoresis apparatus according to claim 1, wherein the evaporation-preventing membrane is made of an elastic material.

10. The capillary electrophoresis apparatus according to claim 1, wherein the evaporation-preventing membrane is made of silicone rubber.

11. The capillary electrophoresis apparatus according to claim 1, wherein the cover is adhered to the container with the use of an adhesive or via ultrasonic fusion bonding.

12. The capillary electrophoresis apparatus according to claim 1, wherein the cover is fixed to the container with the aid of a snap-fit fastener device.

13. The capillary electrophoresis apparatus according to claim 1, wherein the evaporation-preventing membrane has a recess extending along a circumference and an upper end of the container is engaged with the recess.

14. The capillary electrophoresis apparatus according to claim 1, wherein the at least two protruding portions are disposed radially on the outer periphery of the cylindrical section of the capillary hole.

15. A solution reservoir apparatus configured for use in a capillary electrophoresis apparatus comprising at least one capillary, a power supply configured to apply voltage to both ends of the at least one capillary, an optical unit configured to irradiate a sample separated by electrophoresis in the at least one capillary with an excited light and configured to detect fluorescence emitted from the sample, and an autosampler configured to transport the solution reservoir apparatus,
wherein the solution reservoir apparatus comprises:
a container configured to reserve a sample or solution,
a cover having a bore through which the at least one capillary is passed and configured to cover the container,
an evaporation-preventing membrane configured for positioning on the cover, and
a container holder configured to hold the container, wherein the evaporation-preventing membrane comprises at least one projection configured for passing through the bore on the cover, said at least one projection comprises a capillary hole having a cylindrical section, an end bore, and at least two protruding portions provided at the outer periphery of the cylindrical section of the capillary here hole, and wherein the at least two protruding portions are engaged with the bore on the cover when the evaporation-preventing membrane is positioned on the cover.

16. The solution reservoir apparatus according to claim 15, wherein the at least two protruding portions comprise four protruding portions which are disposed radially on the outer periphery of the cylindrical section of the capillary hole.

17. The solution reservoir apparatus according to claim 15 wherein the evaporation-preventing membrane is made of an elastic material, an outer diameter of the at least two protruding portions of the at least one projection is greater than an inner diameter of the bore on the cover, an outer diameter of the cylindrical section of the at least one projection is less than or equal to the inner diameter of the bore on the cover, an inner diameter of the end bore of the at least one projection is less than an outer diameter of the at least one capillary, and an inner diameter of the capillary hole of the evaporation-preventing membrane is greater than an outer diameter of the at least one capillary.

18. The solution reservoir apparatus according to claim 15, wherein the cover is adhered to the container with the use of an adhesive or via ultrasonic fusion bonding.

19. The solution reservoir apparatus according to claim 15, wherein the cover is fixed to the container with the aid of a snap-fit fastener device.

20. The solution reservoir apparatus according to claim 15, wherein the at least two protruding portions are disposed radially on the outer periphery of the cylindrical section of the capillary hole.

21. A capillary electrophoresis apparatus comprising a at least one capillary, an optical unit for irradiating a sample separated by electrophoresis in the at least one capillary with an excited light and detecting fluorescence emitted from the sample, a solution reservoir apparatus for reserving a sample or solution, and an autosampler for transporting the solution reservoir apparatus,
wherein the solution reservoir apparatus comprises a container for reserving a sample or solution, a cover having a bore through which the capillary is passed and covering the container, an evaporation-preventing membrane configured for positioning on the cover, and a container holder for holding the container, wherein
the evaporation-preventing membrane comprises a at least one projection configured for passing through the bore on the cover, said at least one projection comprises a capillary hole having a cylindrical section, an end bore, and at least two protruding portions provided at the outer periphery of the cylindrical section of the capillary hole, wherein the at least two protruding portions are engaged with the bore of the cover when the evaporation-preventing membrane is positioned on the cover.

22. The capillary electrophoresis apparatus according to claim 21, wherein outer diameters of the at least two protruding portions of the at least one projection are greater than an inner diameter of the bore on the cover, an outer diameter of the cylindrical section of the at least one projection is less than or equal to the inner diameter of the bore on the cover, an inner diameter of an end bore of the at least one projection is less than an outer diameter of the at least one capillary, and an inner diameter of the capillary hole of the evaporation-preventing membrane is greater than an outer diameter of the at least one capillary.

23. The capillary electrophoresis apparatus according to claim 21, wherein the at least two protruding portions comprise four protruding portions which are arranged radially on the outer periphery of the cylindrical section of the capillary hole.

24. The capillary electrophoresis apparatus according to claim 21, wherein the at least two protruding portions are disposed radially on the outer periphery of the cylindrical section of the capillary hole.

* * * * *